United States Patent [19]

Gershon et al.

[11] Patent Number: 4,832,486
[45] Date of Patent: May 23, 1989

[54] METHOD AND APPARATUS FOR IN VITRO EVALUATION OF FOCAL LENGTH AND FOCAL LENGTH CHANGES IN LENSES FROM HUMAN AND ANIMAL EYES

[75] Inventors: David Gershon, Tivon, Israel; Jacob G. Sivak, Waterloo, Canada; Ahuva Dovrat, Torrance, Calif.

[73] Assignee: Canadian Industrial Innovation Centre/Waterloo, Waterloo, Canada

[21] Appl. No.: 844,944

[22] Filed: Mar. 27, 1986

[30] Foreign Application Priority Data

Apr. 17, 1985 [CA] Canada .................................. 479405

[51] Int. Cl.$^4$ .............................................. G01B 9/00
[52] U.S. Cl. .................................................. 356/125
[58] Field of Search ................ 356/124, 125, 126, 127

[56] References Cited

PUBLICATIONS

"Spherical Aberration of the Crystalline Lens", J. G. Sivak and R. O. Kreuzer, Vision Res., vol. 23, pp. 59–70, 1983.
"Aging and the Optical Quality of the Rat Crystalline Lens", J. G. Sivak and A. Dovrat, Investigative Opthalmology & Visual Science, vol. 24, pp. 1162–1166, Sep. 1983.

Primary Examiner—F. L. Evans
Attorney, Agent, or Firm—R. Craig Armstrong

[57] ABSTRACT

A method for in vitro evaluation of focal length changes in a lens is disclosed, involving the steps of projecting parallel laser beams through the lens at at least two points, examining the convergence of the beams after exiting the lens to determine the focal length of the lens, and after a period of time, repeating these steps and comparing the focal length. Preferably, a scanning laser is used so that a number of beams pass through different spots on the lens, so that the spherical aberration of the lens may also be determined and compared over time. Apparatus is disclosed for carrying out the method, comprising a carousel plate having a number of spaced holes for receiving lens containers. A carousel drive servo motor rotates the carousel from lens container position to lens container position. A helium-neon laser is mounted horizontally on an X-Y table, and the laser beam is deflected upwardly through a lens held in a lens container. Mirrors provide a video camera with two views of the lens focal point area, the viewpoints being offset from each other by 90 degrees. The video camera signal is fed to a personal computer for analysis. A display monitor and printer are connected to the computer. The software may be directed to display and print the actual video camera image, or to digitize the information and produce a display or printout illustrating the spherical aberration of the lens.

5 Claims, 3 Drawing Sheets

METHOD AND APPARATUS FOR IN VITRO EVALUATION OF FOCAL LENGTH AND FOCAL LENGTH CHANGES IN LENSES FROM HUMAN AND ANIMAL EYES

This invention relates to a method of evaluating changes in the focal characteristics of human and animal lenses in an in vitro lens culture, and to apparatus for carrying out the method.

The lens of the eye has been the centre of intense recent attention, both because of possible benefits related to understanding the causes and means of preventing cataracts and because the continued growth of the lens through life makes it an ideal tissue for the study of aging. The fact that it is avascular and that it is encapsulated inside the eye within an acellular envelope has somewhat simplified handling and maintenance, and has prompted numerous efforts to culture the intact lens.

Any significant alteration in lens water content (and therefore in refractive index) and lens curvatures will have refractive repercussions, and therefore an effect on focal length of the lens. Focal length would thus appear to be a useful index of lens function during culture work.

The present invention involves an evaluation of focal length changes over time, which can have many experimental and practical applications. One particular application, for example, could be as a replacement for the Draize eye irritation test commonly used on rabbits for testing of perfumes and cosmetics. An in vitro method which would replace such testing is obviously desireable, especially if greater accuracy and reliability could be achieved in the process.

Since the lens is an optical device as well as being a biological tissue it is reasonable to expect that the measurement of lens optical quality would be a primary means of monitoring lens function during culture and cataractogenesis research. However, efforts to use the optical properties of the lens as a measure of lens condition have been desultory and largely qualitative in nature. Direct photography of the lens has been the most common approach. In some instances a grid has been photographed through the lens and one group of researchers has developed a shadowgram index of lens transparency. One group has determined lens turbidity by measuring the intensity of a helium-neon laser beam as it passed through various portions of the lens.

Such efforts in the prior art indicate that the main optical interest has been in the detection of obvious cataractous changes in lens transparency. However, it is known that the physical parameters of the lens are sensitive to factors known to affect single cells, and that changes in lens biochemistry begin well before the appearance of pronounced opacities. Variations in refractive state of the eye, presumably due to change in lens volume and curvature, are among the early indications of diabetes mellitus while the addition of a variety of materials (including glucose and xylose) to lens culture media affects lens weight and water content.

In the prior art, split beam lasers have been projected through lenses maintained in a culture medium, the lens focal effects being photographed externally for studying such things as lens physiology and cataractogenesis. The technique does not appear to have been used to study lens focal effects over time or in response to artificial stimuli such as contaminants introduced into the culture media.

The present inventors have developed a method involving projecting laser beams through lenses maintained in vitro and examining the lens focal effects for the analysis of lens aberrations. The method has been used experimentally to demonstrate the imprecise refractive quality of the aged human lens, presumably due to variations in refractive index associated with age related protein aggregation. It has also been used to determine the effect of age on spherical aberration of the rat lens. Apparatus has been developed to permit the use of the method to monitor lens refractive condition during lens culture experiments.

It is an object of the invention to provide a method for examining the current biological state of a lens and if desired, comparing that state to a subsequent state. Such a method would be useful in many research applications, and could offer a replacement for the Draize test.

It is a further object of the invention to provide apparatus for carrying out the method.

In accordance with the method of the present invention there is provided a method comprising the steps of positioning a lens in culture media in a transparent lens container, projecting parallel laser beams through the lens at at least two points, examining the convergence of the beams after exiting the lens to determine the focal length of the lens, and after a period of time, repeating these steps to compare the focal length before and after the period of time.

In accordance with another version of the method, the laser beams are projected through the lens at a number of locations, and the examination of the convergence of the beams determines the spherical aberration of the lens, which may be compared on a before and after basis.

In accordance with the apparatus of the present invention there is provided means for supporting a transparent lens container, a laser beam positioned to direct a beam through a lens mounted in the lens container, a camera for viewing the lens focal area at an angle substantially normal to the lens axis, and means for directing parallel beams from the laser through the lens substantially parallel to the lens axis at at least two points separated from each other as viewed from the camera location.

Further features of the invention will be described or will become apparent in the course of the following detailed description.

In order that the invention may be more clearly understood, the preferred embodiments thereof will now be described in detail by way of example, with reference to the accompanying drawings, in which:

FIG. 4 is a simple sketch representing the image seen by the camera in the preferred apparatus;

FIG. 5 is a sketch similar to that of FIG. 4, but showing spherical aberration;

FIG. 6 is a representation of the appearance of a graph of variation in back vertex power across the lens; and FIG. 7 is a sketch of an alternative embodiment.

Figure 1:
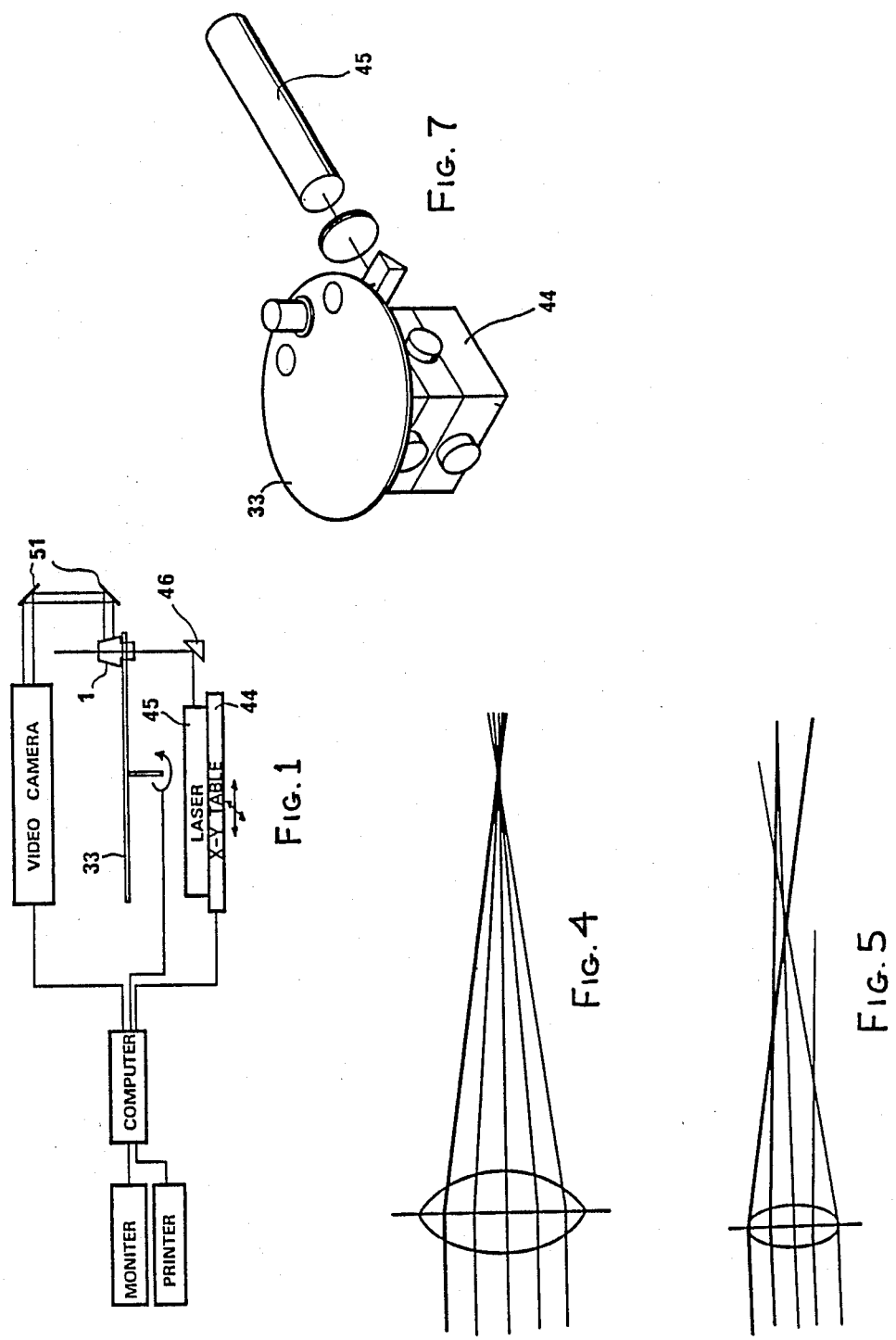
FIG. 1 is a block diagram illustrating the principle of the preferred apparatus of the present invention.
Figure 2:
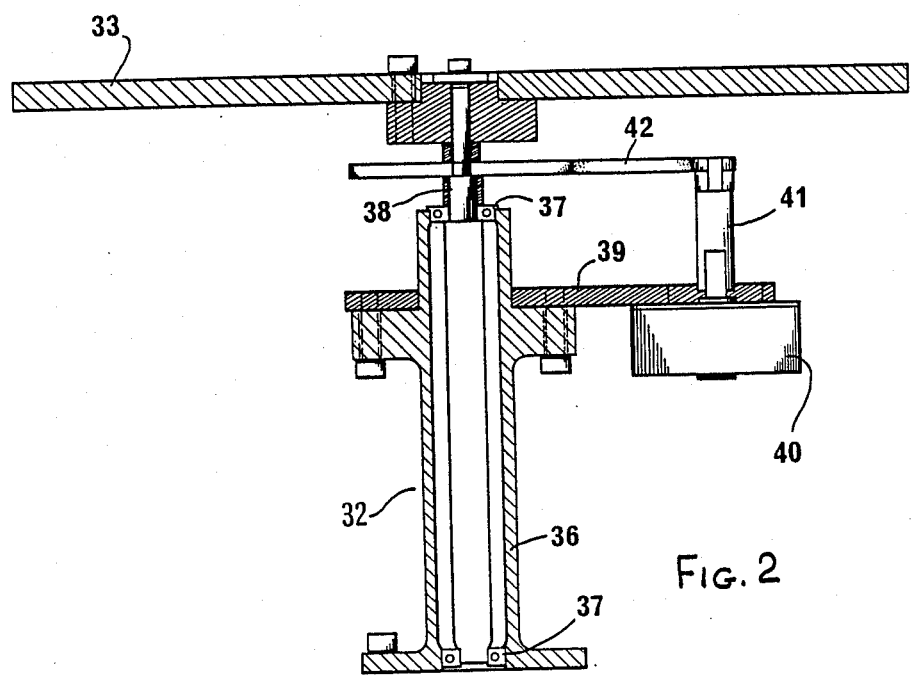
FIG. 2 is an elevation view of the carousel support assembly and carousel.
Figure 3:
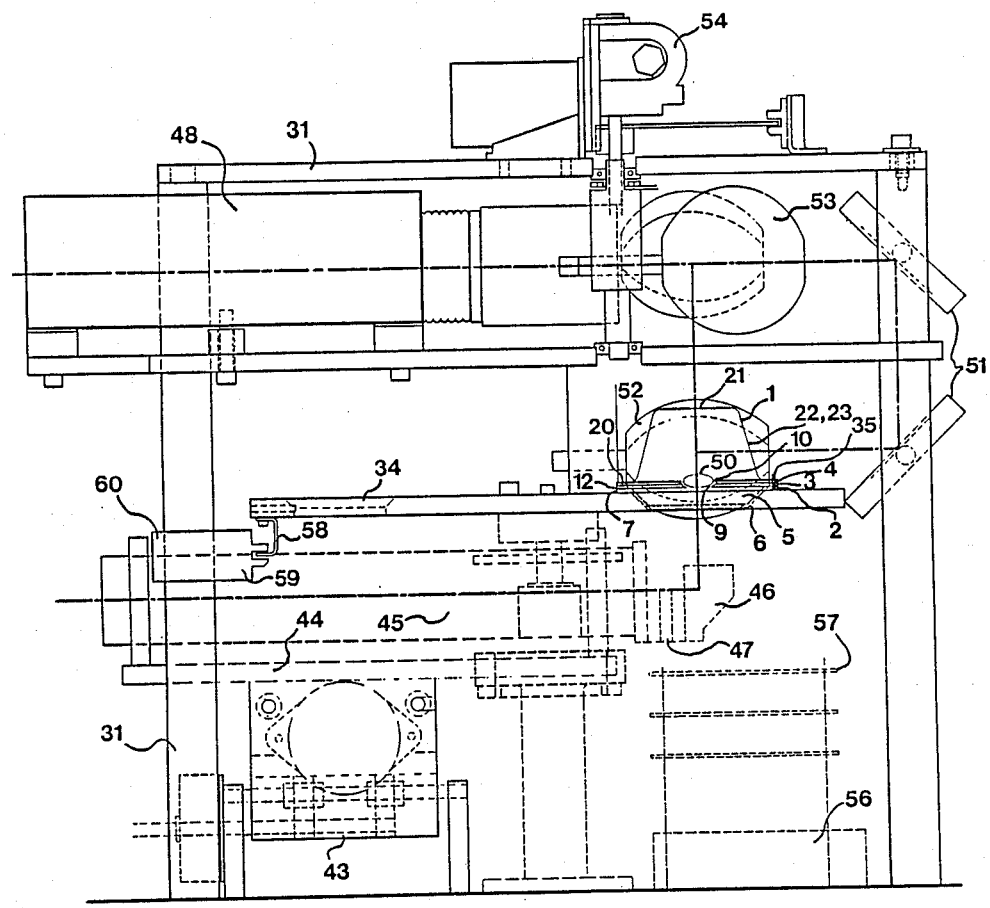
FIG. 3 is an elevation view of the preferred apparatus.

The preferred method of the present invention may be best understood in conjunction with the following description of the preferred embodiment of the apparatus used for carrying out the method.

The apparatus is mounted inside an incubating cabinet 31 so that all aspects of the experiments can take place in a controlled environment. The cabinet is provided with a small heating element (not illustrated) and a calibrated, adjustable thermostat (also not illustrated) covering the range from 20 degrees to 40 degrees Celsius. The cabinet temperature is preferably kept at around 35 degrees Celsius.

Suspended above the base of the cabinet by a carousel support assembly 32 is a carousel plate 33 having a number of spaced holes 34 capable of receiving lens containers 1. The lens containers are described in more detail in a copending patent application entitled "Containers for Culturing and Testing of Vertebrate Lenses", Ser. No. 844,579, filed Mar. 27, 1986, but may be described briefly as follows.

In the preferred embodiment of the lens containers, each of the containers 1 designed to contain a lens 50 consists of a base 2, a lens carrier 3, and a cover 4. The base, lens carrier and cover are all of transparent material such as glass or a transparent plastic (e.g. acrylic or styrene).

The base 2 is circular in top view, and in sectional elevation is in the form of a flanged U-shape. The central depression forms a well 5 having a cylindrical wall 6, which is used for positioning the container in a hole 34 in the carousel 33 for testing. The annular flange 7 then supports the container above the carousel, with the well protruding downwardly into the hole in the carousel and the wall of the well contacting the sidewall of the hole.

The lens carrier 3 is essentially a circular plate with a central aperture 9. The lip 10 of the aperture tapers downwardly in order to support the outer rim of the lens to be tested. The region of the plate near the periphery constitutes an annular flange 12.

The cover 4 has an annular flange 20, and a raised centre section 21 with angled sidewalls 22 connecting the annular flange to the centre section. The sidewalls are not perfectly conical, but rather have two flat sections 23 offset from each other by 90 degrees, which act as viewing ports in the apparatus described in the copending application, the purpose of the flat sections being to minimize distortion.

The base, lens carrier and cover annular flanges 7, 12 and 20 respectively, are of substantially the same diameter, namely about 3.25 inches, and rest in turn on each other and are sealed to each other by any suitable means such as ultrasonic welding or adhesive.

Each annular flange 7, 12 and 20 is provided with a small radial notch (not shown) at its periphery, which is used to position the container properly in the carousel hole 34, the carousel being provided with a pin 35 near the edge of each hole to engage in the notches.

The lens 50 to be studied is centered in the aperture 9 in the bottom of the lens carrier 3. The selected diameter of the hole depends of course on the type of lens to be examined, and would ordinarily range from about 2.5 millimeters for rat lenses to up to about 13 millimeters for cow lenses, for example.

Lens organ culture is usually carried out by immersing the entire lens in a single culture medium. However, the lens container has been designed so that the anterior and posterior lens surfaces may be exposed to separate media, one contained between the base and the lens carrier element, and the other contained between the cover and the lens carrier element. In order for this to be accomplished, the rim of the lens must be glued to the lip 10 of the aperture, using for example a silicone adhesive such as Sylgard R (Trademark of Dow Corning Corp.). The maintenance of an effective separation between the lens surfaces can be confirmed by the observation of steady asymmetry in electrical potential (usually 22 to 26 mV) when electrodes are placed in the separate media regions with an experimental lens in place, using the technique described by Duncan et al, (1977) "A simple chamber for measuring lens assymetry potentials", Exp.Eye.Res. 25, 391-398.

Thus it is possible to compare the effect of using a single medium (M199 with Earle's salts and 5% fetal calf serum, for example) to, for example, a situation in which the anterior lens is bathed in M199 while the posterior surface is in contact with a vitreous medium. An appropriate mixture of atmospheric gases (90% $N_2$, 5% $CO_2$, 5% $O_2$) can be admitted into the incubator during each experiment if desired.

This ability to contact the anterior and posterior sides of the lens with different media is useful not only for the simulation of real conditions, but also and particularly for such uses as subjecting one side of the lens to a toxic substance to observe the effect, as would be the case in using the method as a replacement for the Draize test.

The lens can be maintained in culture in the lens container for periods of 30 days or more, so that the lens focal effects can be monitored over a period of time, as desired in accordance with the method of the present invention.

The carousel support assembly 32 comprises a shaft support member 36 which is bolted to the cabinet base, and upper and lower bearings 37 which support a rotatable shaft 38 to which the carousel plate 33 is attached for rotation. Attached to the shaft support member is a motor support 39, on which a carousel drive servo motor 40 is attached. The servo motor has a drive shaft 41 extending parallel to the carousel shaft 38. A drive belt 42 runs around the drive shaft and the carousel shaft to drive the carousel plate from the servo motor.

Also mounted on the incubator base, beneath the carousel, is an X-Y table assembly 43, with a table 44 on which a helium-neon laser 45 of approximately 0.5 to 1 mW power is mounted. The laser is horizontally mounted, but has a prism assembly 46 attached at its output, so that the laser beam is deflected upwardly. Several filter slots 47 are provided between the laser output and the prism, so that the laser beam may be filtered if and as desired.

By appropriate positioning of the X-Y table 44 and the lens containers 1 in the carousel holes 34, the laser beam may be projected up through a lens held in a lens container.

Also installed in the cabinet, above the carousel, is a horizontally oriented video camera. Mirrors are mounted within the cabinet in order to provide the video camera with two views of the lens focal point area within the lens container being examined, the viewpoints being offset from each other by 90 degrees. A first pair 51 of fixed mirrors are positioned so that the lens focal area 55 is normally viewed from one position in the horizontal plane. A movable mirror 53, driven by a second servo motor 54, is positionable in front of the video camera so that instead of receiving its image from the first pair of mirrors 51, the video camera receives its image via a second pair 52 of fixed mirrors and this movable mirror. This second image path provides a view of the lens focal area from a viewpoint at 90 degrees in the horizontal plane from the first viewpoint. Sensing photodiodes 60 are provided for detecting the first and alternate positions for the movable mirror, so that the mirror position is known at any given time.

The video camera signal is fed to a personal computer for analysis. A display monitor and printer are connected to the computer. The software may be directed to display and print the actual video camera image, or to digitize the information and produce a display or printout illustrating the spherical aberration of the lens, in the form of a graph showing the variation in back vertex power, such as the one illustrated in FIG. 6. Back vertex power $Fv^1$ equals $n/fv^1$, where n is the index of refraction of the medium and $fv^1$ is the back vertex distance.

Also mounted in the cabinet are a laser power unit 56 and circuit boards 57.

In operation, a lens container 1 is positioned appropriately for viewing by the video camera 48, under the action of the carousel servo motor 40. The carousel is provided with a small bracket 58 which extends down from the carousel plate to pass through an opening in a sensing photodiode assembly 59, so that the home position of the carousel plate may be detected so that the lens containers may be properly positioned.

The laser 45 is then properly positioned under the laser container, with each experimental lens in turn being centered independently beneath the laser. Each lens to be tested is centered by scanning the laser across the lens in one direction until the beam passes undeviated through the lens, indicating the location of its optic axis. The moveable mirror 53 is then moved to its alternate position, and the laser scans across the lens again to detect the lens centre from that viewpoint. This establishes the location of the lens axis, having established two central planes at right angles to each other. The X-Y table 44 is then translated so that the laser scans across the lens. With the movable mirror in one position, the scanning is effected, and then the scan pattern is repeated with the movable mirror in the alternative position. This centering is effected under the control of the software.

Despite a relatively broad laser beam diameter on exit from the laser, a very fine line can be seen when viewing the beam path through the lens, because the fringes of the beam are less intense than the centre, and are filtered out in passing through the culture medium and the lens. Neutral density filters, a low-power condensing lens in front of the laser, or a different power laser could be used if the line is so broad as to complicate the examination and analysis. A fine line permits a very fine determination of the lens focal effects to be made.

The automated techniques made possible by the apparatus enable the method to be carried out with greater data throughput and with consistent data analysis.

As can be gleaned from the above description of the apparatus, the method of the present invention in its most basic form involves the steps of positioning the lens in culture media in a transparent lens container, projecting parallel laser beams through the lens at at least two points, examining the convergence of the beams after exiting the lens to determine the focal length of the lens, and after a period of time, repeating these steps and thereby comparing the focal length before and after the period of time. Preferably, however, a scanning laser is used so that a number of beams pass through different spots on the lens, so that the examination of the convergence of the beams determines the spherical aberration of the lens, so that the spherical aberration of the lens before and after the period of time may be compared. Smaller changes in lens focal characteristics may thus be detected than by merely considering lens focal length.

Thus, to apply the method, a sample lens is scanned with the laser and the data is recorded. The lens is then maintained in culture for a period of time, for subjection to natural or artificial aging, or to substances such as perfumes or cosmetics injected into the culture medium or media. The lens is then scanned with the laser again, and the data is recorded and compared with the earlier data to note any changes in lens focal length, spherical aberration, or both.

It will be appreciated that the above description relates to the preferred embodiments by way of example only. Many variations on the invention will be obvious to those knowledgeable in the field, and such obvious variations are within the scope of the invention as described and claimed, whether or not expressly described.

For example, it should be apparent that similar results could be achieved by projecting multiple or split laser beams through the lens to analyze focal effects, rather than a single beam which scans across the lens.

As another example, FIG. 7 illustrates an alternative embodiment in which the carousel assembly rather than the laser is mounted on the X-Y table.

The embodiments of the invention in which an exclusive property or privilege is claimed are defined as follows:

1. A method for in vitro evaluation of changes in focal characteristics of a vertebrate eye lens over time in response to a stimulus, comprising the steps of:
   a. positioning said lens in culture medium in a transparent lens container;
   b. projecting parallel laser beams through said lens at at least two points;
   c. examining the convergence of said beams after exiting said lens to determine focal characteristics of the lens;
   d. applying a stimulus to said lens in said culture medium;
   e. after waiting a period of time, repeating steps a through c; and
   f. comparing said focal characteristics before and after said period of time; whereby changes in focal characteristics over said period of time in response to said stimulus may be detected.

2. A method as recited in claim 1, in which said laser beams are projected through said lens at a number of locations, and in which said examination of the convergence of said beams determines the spherical aberration of said lens, and in which the spherical aberration of said lens before and after said period of time may be compared.

3. A method as recited in claim 1 where said stimulus is the introduction of a contaminant into the culture medium.

4. A method as recited in claim 2 where said stimulus is the introduction of a contaminant into the culture medium.

5. Apparatus for evaluation of vertebrate eye lens focal characteristics changes over time, comprising:
   a carousel for supporting a plurality of transparent containers for each supporting a lens with its axis substantially vertically oriented;

indexing means for stepping said carousel to sequentially position consecutive lens containers in a viewing area;

a laser beam producing means positioned to direct a laser beam through said viewing area substantially parallel to the lens axis;

a camera directed at the viewing area for viewing at an angle substantially normal to the lens axis;

means for translating said laser beam to direct said laser beam through said viewing area and said lens at at least two points separated from each other as viewed from the camera location; and data recording means for recording data from the camera image and correlating that data to the lens container in the viewing area, whereby said data may be stored for subsequent comparison with data recorded from later evaluation of the same lens.

* * * * *